United States Patent
Everhard

(10) Patent No.: US 11,840,926 B2
(45) Date of Patent: Dec. 12, 2023

(54) NON-INVASIVE TIME-BASED SAG TESTING APPARATUS

(71) Applicant: Baker Hughes Oilfield Operations LLC, Houston, TX (US)

(72) Inventor: Eliah M. Everhard, Spring, TX (US)

(73) Assignee: BAKER HUGHES OILFIELD OPERATIONS LLC, Houston, TX (US)

( * ) Notice: Subject to any disclaimer, the term of this patent is extended or adjusted under 35 U.S.C. 154(b) by 0 days.

(21) Appl. No.: 17/488,000

(22) Filed: Sep. 28, 2021

(65) Prior Publication Data
US 2023/0093958 A1   Mar. 30, 2023

(51) Int. Cl.
*E21B 49/00* (2006.01)
*G01N 9/36* (2006.01)
*G01N 11/00* (2006.01)
*G01N 11/14* (2006.01)
*G01N 15/06* (2006.01)

(52) U.S. Cl.
CPC ........... *E21B 49/005* (2013.01); *G01N 9/36* (2013.01); *G01N 11/14* (2013.01); *G01N 15/06* (2013.01); *G01N 2011/0093* (2013.01)

(58) Field of Classification Search
CPC ............ E21B 49/005; G01N 15/04; G01N 2011/0093
See application file for complete search history.

(56) References Cited

U.S. PATENT DOCUMENTS

| | | | |
|---|---|---|---|
| 2,845,793 A * | 8/1958 | Cardwell, Jr. | ......... B01D 21/30 73/61.65 |
| 5,086,646 A | 2/1992 | Jamison et al. | |
| 6,330,826 B1 | 12/2001 | Meeten | |
| 6,584,833 B1 | 7/2003 | Jamison et al. | |
| 7,845,212 B1 | 12/2010 | Bi | |
| 8,511,150 B2 | 8/2013 | Lucas et al. | |
| 9,719,965 B2 | 8/2017 | Mandal et al. | |
| 9,995,619 B2 | 6/2018 | Parker et al. | |
| 10,139,328 B2 | 11/2018 | Ladner et al. | |
| 10,712,223 B2 | 7/2020 | Stanley et al. | |
| 10,914,664 B1 | 2/2021 | Miller et al. | |

FOREIGN PATENT DOCUMENTS

| | | | |
|---|---|---|---|
| CN | 103267714 A | 8/2013 | |
| WO | 1988006720 A | 2/1988 | |
| WO | WO-2021154313 A1 * | 8/2021 | ............. C09K 8/032 |

OTHER PUBLICATIONS

Omland, Tor H. et al., Detection Techniques Determining Weighting Material Sag in Drilling Fluid and Relationship to Rheology, In: Annual Transactions of the Nordic Rheology Society, 2007, vol. 15, pp. 1-9.

Murphy, R. et al., Apparatus for Measuring the Dynamic Solids-Settling Rates in Drilling Fluids, In: SPE Annual Technical Conference and Exhibition, Sep. 2006, pp. 1-9.

* cited by examiner

*Primary Examiner* — John Fitzgerald
(74) *Attorney, Agent, or Firm* — Crowe & Dunlevy, P.C.

(57) ABSTRACT

Time-based sag in a fluid can be measured non-invasively using a time-based sag testing apparatus by measuring the change in rotational inertia over time of fluid having no initial density gradient and a center of mass initially coincident with its geometric center.

5 Claims, 3 Drawing Sheets

NON-INVASIVE TIME-BASED SAG TESTING APPARATUS

TECHNICAL FIELD

The present invention relates to methods and apparatus for determining the sag of fluids, and more particularly relates, in one non-limiting embodiment, to methods and apparatus for non-invasively determining the sag of drilling fluids as a function of time.

TECHNICAL BACKGROUND

A problematic phenomenon in well fluids that contain suspended particles, such as drilling muds, is "sag". Sag occurs, for example, when circulation of the fluid is stopped for a period of time, e.g. when the drill string must be tripped from the well, and is caused by the resulting settling or stratification of the fluid whereby "heavy spots" develop. Sag can also involve movement or shifting of the fractions, particularly the "heavy spots," where components such as barite have become concentrated. Sag may not occur throughout an entire well, but nevertheless, its occurrence in even a small section of the well can cause the problems referred to below.

Such settling is not particularly problematic if the well is a vertical or near vertical. The magnitude of the problem is also relatively small if the well, or the section of the well in question, is nearly horizontal. However, if the well or a section thereof has a relatively high deviation angle (i.e. angle with respect to vertical), but falling well short of 90°, sag problems can become particularly severe. The advent and recent strides in directional drilling, which have resulted in relatively highly deviated wells, e.g. wells with deviation angles of 20° or more, has brought sag problems currently into focus in the industry.

More precisely, sag can be defined as the settling of particles in the annulus of a well, which can occur when the mud is static or being circulated. Because of the combination of secondary flow and gravitational forces, weighting materials (e.g., barite) can settle (sag) in a flowing mud in a high-angle well. If settling is prolonged, the upper part of a wellbore will lose mud density, which lessens the hydrostatic pressure in the hole, so an influx (a kick) of formation fluid can enter the well.

Among other problems caused by sag phenomena are sticking of drill pipe, difficulty in re-initiating and/or maintaining proper circulation of the fluid, possible loss of circulation, and disproportionate removal from the well of lighter components of the fluid.

Prior efforts to control sag phenomena have included modification of muds or drilling fluids by altering parameters such as the yield point, which were believed to affect sag. However, the basis for such variations has been mainly actual field experience which, because of the inability to know with certainty precisely what is occurring downhole, involved a certain amount of guess work.

Techniques have been developed for testing and/or analyzing other properties of well fluids in a laboratory environment, but many of these were not intended to analyze sag, and none of them has been completely satisfactory for that purpose (e.g., in optical transmission-based solutions). Typically, sag testing of fluids involves allowing a sample to age for a fixed amount of time and then destructively examining the amount of sag that has occurred by measuring the density at discrete levels in the fluid, i.e., opening the test cell, removing and sampling the top third of the fluid, removing and sampling the middle third of the fluid, and removing and sampling the lower third of the fluid. This test method is more binary in that it only indicates that sag has occurred after a certain time interval and requires several tests at specific time intervals to be run to determine the time that sag has occurred, with each test necessitating the assembly and subsequent disassembly of the fluid via the methodology described above.

U.S. Pat. No. 5,086,646 describes a method and apparatus for analyzing sag phenomena in well fluids wherein an elongate container containing a sample of a fluid to be tested is mounted at an angle with respect to vertical on a force responsive device which provides a measurable, variable indication of the center of mass of the container. The angle is chosen to correspond to that of a well deviation angle for which testing is to be done, and the sample may be subjected to heat and pressure to further simulate downhole conditions. The aforementioned indication provided by the force responsive device is repeatedly measured and functionally related to time.

It would be desirable in the art to develop a test apparatus and method to non-invasively track the kinematic change in the mass distribution of fluid that would eliminate the need for multiple tests, as well as to be able to track the rate at which sag is occurring.

SUMMARY

There is provided in one non-limiting an apparatus for non-invasively determining time-based sag of a fluid mass, the apparatus having a test cell having an inner chamber; a support stand having a pivot rotatably engaging the test cell, where the test cell rotates about a lateral axis intersecting the pivot; a rotator configured to rotate the test cell about the pivot, the rotation being from a first point and a second point; and a torque sensor configured to estimate a torque value associated with the test cell at at least one point during rotation inclusively between the first point and the second point, where the torque value represents a change in a location of a center of mass of the fluid mass. In operation, the test cell contains a liquid mass, and the original center of mass of the test cell is determined with the liquid mass present.

There is additionally provided in another non-restrictive version, a non-invasive method for measuring time-based sag in a fluid, where the method includes providing a test cell having an inner chamber, where the inner chamber contains a liquid comprising mass, where the test cell comprises an original center of mass when the test cell is in an initial vertical position; after a time period sufficient for fluid sag to occur, rotating the test cell to an angle with respect to vertical from a first point to at least one point between the first point and a second point; measuring the torque of an angular moment of inertia about the original center of mass; and using the measured torque to determine the distance from the center of rotation to a resultant center of mass, the distance being directly proportional to time-based sag.

Figure 1:
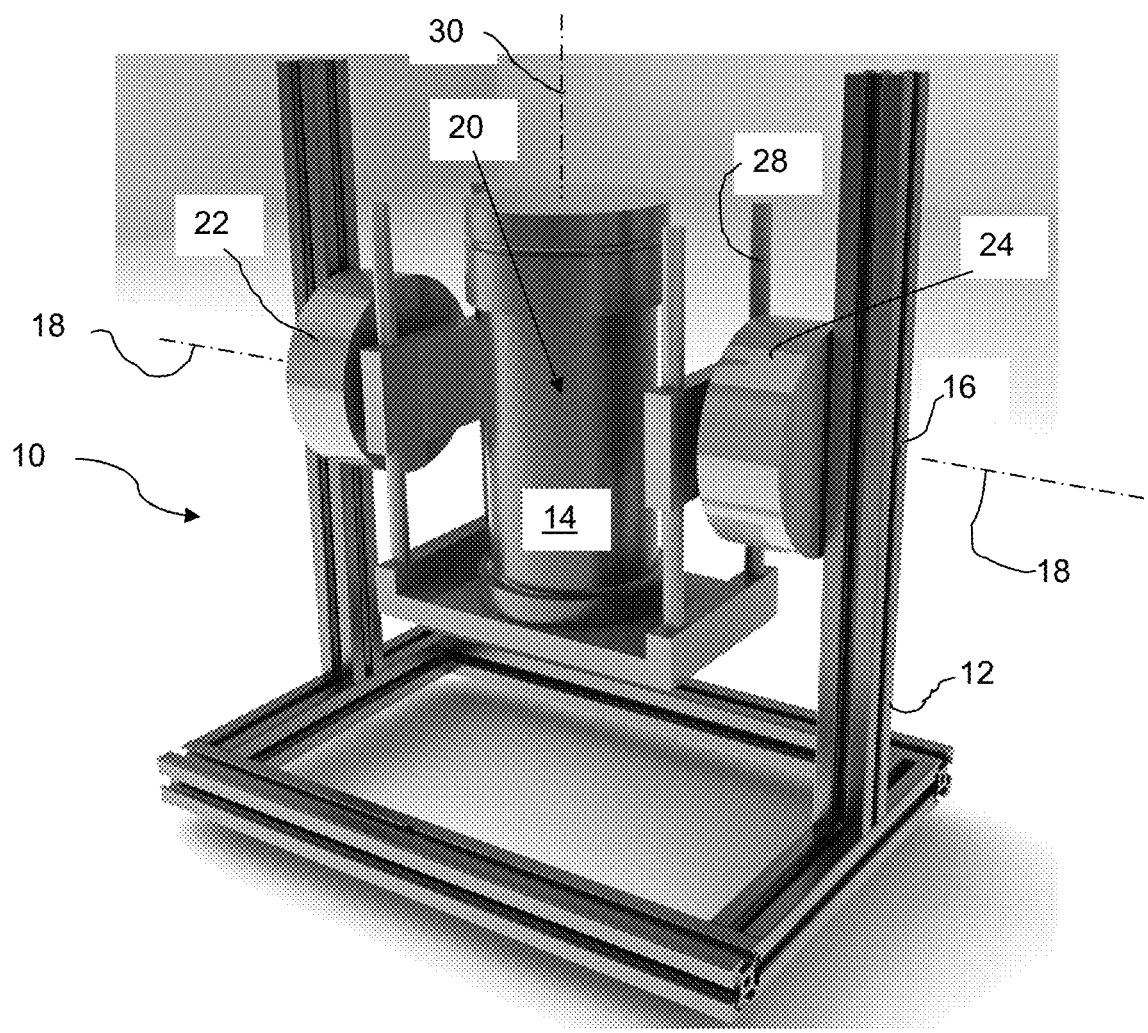
FIG. 1 is a schematic isometric view of one non-limiting embodiment of the non-invasive time-based sag testing apparatus described herein.

It will be appreciated that the Figures are schematic and that many details have been removed or simplified for clarity, and thus the invention is not necessarily limited to the embodiments depicted in these Figures.

DETAILED DESCRIPTION

The present invention relates to a non-invasive time-based sag testing apparatus and a method of using it that allows for the combination of several tests that currently take many days and many separate test cells of fluid to be prepared. Using conventional techniques to determine whether a fluid has sagged after one, three, five, seven, or more days, a sample for each of these tests has to be prepared and destructively analyzed to determine that sag has occurred. There are not very many accurate methods for determining the exact density gradient profile.

By setting a test cell into the apparatus fitted with a torque sensing instrument (or sensor) described herein, the controller initially identifies the center of mass of the cell by adjusting the axial position so that angular motion is constrained about the center of mass. This is recorded and will be the initial reference point of the center of mass. Over time, if sag occurs, this mass center will translate in one direction, and the sensor in the apparatus can measure this shift in either the change in angular acceleration required to rotate or move the cell about its original center of mass, or a static torque imparted on the sensor due to the displacement of the center of mass when the cell is displaced to a small but sufficient angle. In one non-limiting embodiment identifying the original center of mass could be optional. However, identifying the original center of mass will make for a cleaner distinction between the torque induced by the shifted center of mass. The change in torque as measured relative to an initial point of rotation coincident with the center of mass can introduce less error, but can generally be referenced from any initial point of rotation.

Measuring this translation of the center of mass means that the same single sample can be tested over multiple time intervals to characterize the rate and nature of sag. By virtue of a single sample preparation, much fewer person-hours are required, and less product is consumed.

Additionally, there is a large area of study that expands when the sag profiles can be characterized in this matter. As non-limiting examples, this research could indicate whether there is a linear or non-linear rate of sag, or determine the effect of temperature on the rate of sag. These are all characteristics of a drilling mud's "sag profile".

While sag can theoretically occur in any fluid that contains suspended particles which can gravitationally separate out over time, as previously discussed, it is a particular issue for drilling muds used in hydrocarbon drilling operations, especially fluids that contain significant amount of suspended solids or particles, emulsified water and/or oil, intentionally included solid additives include weighting agents or materials used to increase the density of the drilling fluid, or any other additive with different densities than those of any other fluid component.

Shown in FIG. 1 is a schematic isometric view of one non-limiting embodiment of the non-invasive time-based sag testing apparatus 10 described herein illustrating a support stand 12 holding a test cell 14. The support stand comprising a pivot 16 for rotating the test cell 14 about a lateral axis 18 of the test cell, the lateral axis 18 being coincident with longitudinal axis 30 of the test cell 14. The test cell 14 has a length and inner chamber (not shown), where the inner chamber contains a liquid mass (not shown). In a non-limiting embodiment, the liquid mass is a drilling fluid. In non-limiting embodiments, pivot 16 may be an axle, a pin, a hinge, or other mechanism that can be configured to rotate about an axis, in particular lateral axis 18.

The non-invasive time-based sag testing apparatus 10 also has a rotator 22 configured to rotate the test cell about pivot 16 and a torque sensor 24 configured to detect a shift in the original center of mass 20 to a resultant center of mass 26 by measuring either the torque about the pivot 16, or the change of an angular moment of inertia about an initial center of rotation 20. The original center of mass 20 and the resultant center of mass 26 are better illustrated with respect to FIGS. 4 and 5 discussed below. The rotator 22 does not have to rotate the test cell about the lateral axis 18 very far. Indeed, less than 90° from vertical is sufficient. This rocking action should be slow and reversible. That is, the test cell 14 should be initially positioned so that its longitudinal axis 30 is vertical. After a period of time sufficient for sag to occur, the rotator 22 rotates test cell 14 to an angled position, in one non-limiting embodiment less than 90° from vertical. This angle can simulate the angle of a deviated wellbore. A repeated rocking back-and-forth is not needed or required. The rotator may be a motor, servo motor, stepper motor, or other rotating mechanism that provides position control of the test cell 14.

The torque sensor 24 is necessary to measure either a) the torque as the product of force x distance, i.e., the amount of force the new center of mass 26 is imparting at a particular distance around the center of rotation, or b) the angular moment of inertia (resistance to rotation) that the cell/fluid combination with a shifted and distinct density distribution now has compared to its original angular moment of inertia. It will be appreciated that the torque sensor 24 is not required to be in the location shown in FIGS. 1-3, nor is it necessary to have the shape shown. The torque sensor 24 can be in any location on the apparatus 10 and be of any shape so long that it can measure either a) and/or b).

In one non-limiting embodiment, the inner chamber of the test cell 14 is completely filled with the fluid. That is, it has no vapor or empty space, no air or gas.

As used herein, a vertical axis is an axis aligned with gravity and a lateral axis is normal to the vertical axis. When the test cell is operatively connected to the test stand, a longitudinal axis of the test cell is aligned with the vertical axis. As used herein, the terms "aligned" and "coincident" generally refer to an geometric arrangement where two features are parallel, "co-linear" and/or "co-planar."

In another non-restrictive version, the support stand has an elevator 28 configured to move the test cell 14 along a longitudinal axis 30 of the test cell 14. Elevator 28 can move the test cell 14 so that the pivot 16 is coincident with the original center of mass 20, or any other point on axis 30 within the mechanical limits of the apparatus. There may also be optionally provided a heater (not shown) thermally coupled to the liquid mass in the inner chamber of the cell 14 for heating the liquid mass in the inner chamber. Further, there may also be optionally provided a pump, pressurizer, or other mechanism (not shown) in pressure communication with the liquid mass in the inner chamber for subjecting the liquid mass in the test cell 14 to pressure. Additional suitable heating techniques include, but are not necessarily limited to, conduction via heat tracing; convection via an oven; and induction heating coil around the test cell 14. Additional suitable pressurizing techniques include, but are not necessarily limited to, direct gas pressure, and an incorporated cell bladder.

Figure 2:
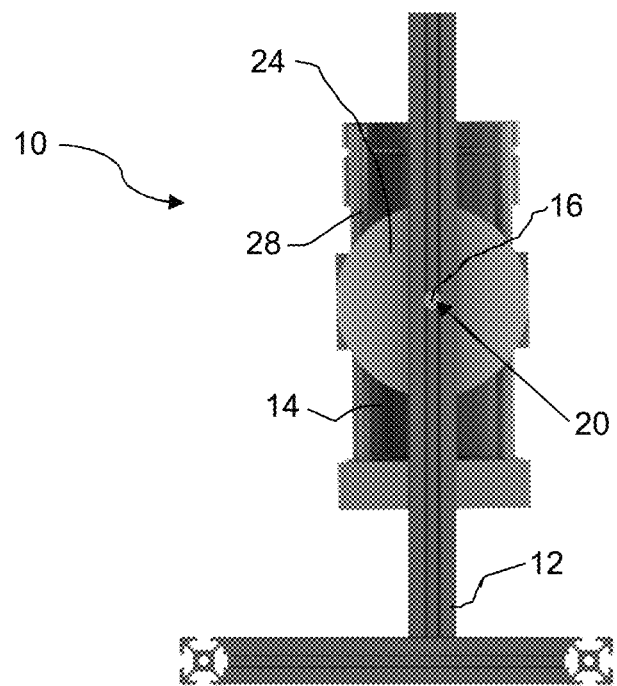
FIG. 2 is a schematic right-side view of the non-invasive time-based sag testing apparatus of FIG. 1.

Shown in FIG. 2 is a schematic right-side view of the non-invasive time-based sag testing apparatus 10 of FIG. 1 where the same reference numerals refer to the same parts and elements of the apparatus 10. In both FIGS. 1 and 2 the test cell 14 is shown in an upright position, which is also the starting position for the method described herein.

Figure 3:
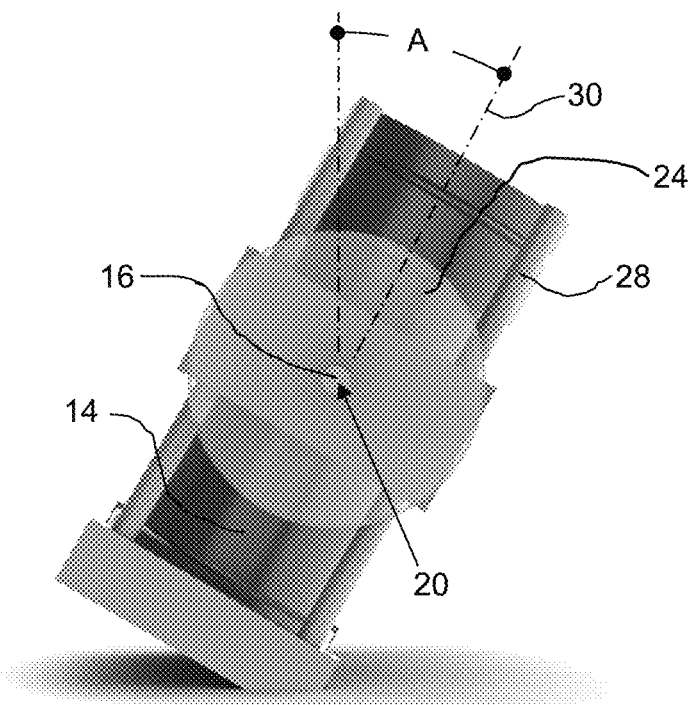
FIG. 3 is a schematic right-side view of the non-invasive time-based sag testing apparatus of FIG. 1 without the support stand.

Shown in FIG. 3 is a schematic right-side view of the non-invasive time-based sag testing apparatus 10 of FIG. 1 without the support stand 12 where the test cell 14 has been rotated about the pivot 16 and positioned at an angle A with respect to vertical. Angle A is less than 90° in one non-limiting embodiment.

Figure 4:
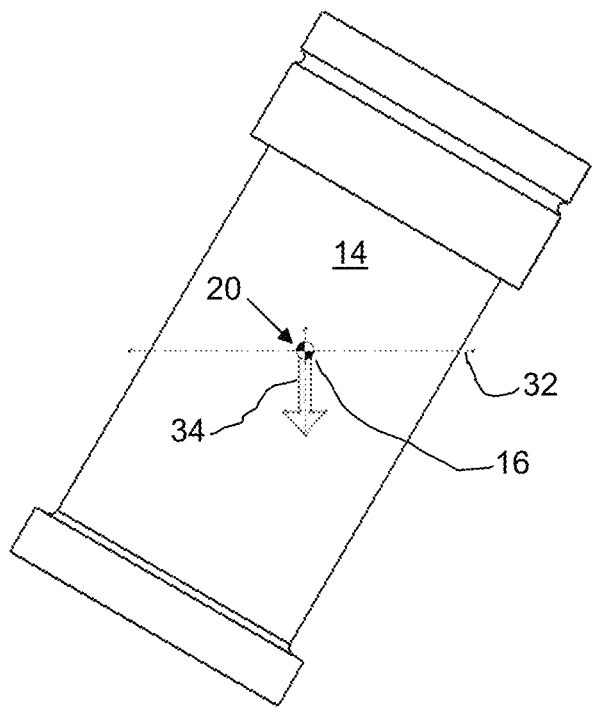
FIG. 4 is a schematic diagram of one non-limiting embodiment of a test cell of non-invasive time-based sag testing apparatus described herein showing an original center of mass.

FIG. 4 is a schematic diagram of one non-limiting embodiment of a test cell 14 of non-invasive time-based sag testing apparatus 10 described herein showing an original center of mass 20, which is coincident with the lateral axis 18 and pivot 16 as shown in FIGS. 1, 2, and 3, discussed above. The force due to gravity is acting through the center of mass in the direction of the arrow 34. The horizontal plane is shown at 32. The position of test cell 14 shown in FIG. 4 is that just as test cell 14 is rotated at angle A to the position shown with no density gradient present in the fluid, i.e., prior to any displacement of center of mass. Both types of these measurements will/can be made: 1) the force at a particular distance from the center of rotation that the new center of mass will impart about the center of rotation when the cell is held statically at an angle other than vertical, and 2) the angular acceleration required to move the cell from vertical to a specific angle at constant angular velocity.

Figure 5:
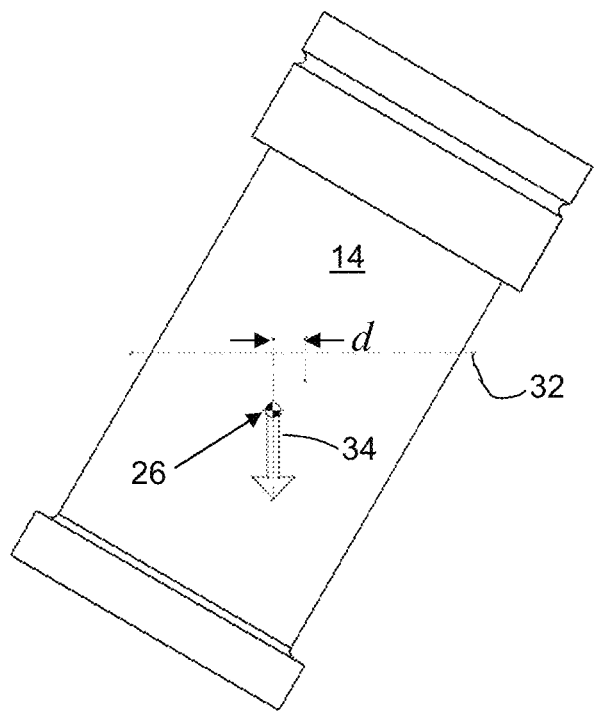
FIG. 5 is a schematic diagram of the test cell of FIG. 4 showing a resultant center of mass after the passage of time.

FIG. 5 is a schematic diagram of the test cell of FIG. 4 showing a resultant center of mass 26 after the passage of time where the center of mass has moved from the original point 20 to resultant center of mass 26. In other words, the liquid mass has experienced sag. The horizontal component of the distance from the original center of mass 20 to the resultant center of mass 26, is length l as shown in FIG. 5. The force at a point of distance d from the center of rotation that the new center of mass will impart about the center of rotation when the cell is held statically at an angle other than vertical is measured with torque sensor 24, as is the force necessary to move test cell 14 from the vertical starting position to the angled position in FIG. 4.

In practicing the method for measuring time-based sag in a fluid using the non-invasive time-based sag testing apparatus 10, the test cell 14 is filled with the test liquid (not shown), where the test cell 14 is in the initial vertical position shown in FIGS. 1 and 2, where the longitudinal axis 30 of the test cell 14 is also vertical and normal to horizontal plane 32. The volume of the test cell 14 is completely filled with the liquid mass; in other words, the volume has no vapor or gas phase present, i.e., no empty space. The test liquid mass is initially homogeneous. The initial, homogeneous density of the liquid mass would have been measured before the test cell 14 was filled and is thus known and would be assumed to be initially consistent everywhere throughout the fluid. A liquid mass that remains homogeneous does not experience sag, even if it is angled or tilted by apparatus 10. At this point in the method, time=$t_0$, or the initial starting time. The test cell comprises an original center of mass 20 which is coincident with the pivot 16 of the apparatus 10 and coincident with the lateral axis 18.

After a time period sufficient for fluid sag to occur, in other words time=final or $t_f$, the test cell 14 is rotated or moved about lateral axis 18 of the test cell 14 on the pivot 16 of the testing apparatus 10 to an angle A with respect to vertical, the lateral axis 18 being coincident with the pivot 16. Fluid mass sag has occurred between $t_0$ and $t_f$. This rotation or movement is done relatively slowly; that is, the cell 14 is rotated a single time at a very low rate perhaps on the order of 1°/second, to give a non-limiting example. Only a small angular displacement is needed; the test cell 14 does not completely revolve around lateral axis 18. The angle A can simulate the angle of a deviated wellbore. For a static test, the test cell 14 is only held at angle A for sufficient time to obtain the measurement, and then returned to the vertical position. The torque τ about the original center of mass 20 relates to how far the new or resultant center of mass 26 has moved.

Stated another way, the rotator 22 is configured to rotate the test cell 14 about the pivot 16 between a first point and a second point across an arc. The torque sensor 24 is configured to estimate a torque value associated with the test cell at at least one point during rotation inclusively between the first point and the second point. "Inclusively" in this context means the first point and the second point are included. In one non-limiting embodiment the arc between the first point and the second point is less than 90°. In another non-limiting embodiment, the first point may be represented by the position of test cell 14 as shown in FIGS. 1 and 2, and the second point may be represented by the position of test cell 14 as shown in FIGS. 3, 4, and 5.

The torque τ about the original center of rotation 20 is measured by the torque sensor 24. In one non-limiting embodiment, this is done by determining sag as a function of the change in center of mass over time from the equation:

$$\tau = c \cdot d$$

where τ is the measured torque, c is the measured force acting through the resultant center of mass 26, and d is the horizontal component of the distance from the resultant center of mass 26 to the original center of mass 20. Distance d may be inferred by use of the parallel-axis theorem:

$$I = \bar{I} + md^2$$

where I is the moment of inertia of the cell about the center of rotation or pivot 16, $\bar{I}$ is the moment of inertia of the cell with respect to the lateral axis 18 which is also the original centroidal axis and which is parallel to the actual axis of rotation 16 and resultant center of mass 26, m is the mass of the cell, and d is the distance between the two axes. The distance d is determined mathematically to locate the resultant center of mass 26. The distance d is directly proportional to time-based sag of the liquid mass. Standards of typical density distributions can be modeled for comparison to measured values.

As mentioned, in one non-limiting embodiment, angle A is less than 90°. In another non-restrictive version, the liquid mass in the test cell 14 is heated using a heater, e.g., oven, induction, heat trace or other suitable mechanism, to heat the liquid mass to a predetermined test measurement. In a different non-limiting embodiment, the liquid mass is pressurized or subjected to using a pump to subject the test cell 14 to a high-test pressure. The liquid mass in test cell 14 may of course be subjected to pressure and heated simultaneously to further simulate the downhole conditions of a wellbore.

In another non-limiting embodiment, the displacement of the center of mass is determined by comparing the measured torque to a set of reference standards. In more detail, there would be a set of model density distributions created and measured as reference standards (i.e., simulated density distributions with strata of different known density gradients). In one non-limiting embodiment the test cylinder would be filled with 1" (2.54 cm) thick layers of rubber of different densities, perhaps with large steel balls in some layers to achieve higher weights. Materials other than rubber layers or steel balls could be used, for instance elastic polymers and glass weights. The moment of these standards on the center of rotation could be compared with the moment of the test cell, thus indicating the displacement of the center of mass. In one non-limiting embodiment, the fluid in the liquid mass includes, but is not necessarily limited to, drilling fluids, drill-in fluids, workover fluids, displacement fluids, treatment fluids, stimulation fluids (which include, but are not necessarily limited to fracturing fluids, acidizing fluids, and the like), or any other fluid used in well construction typically consisting of a plurality of components of different densities. The liquid mass would not ordinarily encompass completion fluids because completion fluids do not ordinarily contain particles, nevertheless the apparatus and method described herein could be used to measure whether a saturated brine has components that precipitate out as a function of concentration, pressure, temperature, etc. and combinations of these factors.

In one non-limiting embodiment, to give some sense of scale, the size of the non-invasive time-based sag testing apparatus 10 would be approximately 3 feet by 3 feet (about 0.9×0.9 meters) or less. In general, the smaller the apparatus 10 the better because it would take up less space and the amount of liquid mass sample needed would be less. Alternatively, more test cells 14 could be incorporated into a single testing apparatus 10 if each test cell 14 were smaller.

In another non-restrictive version, the test cell 14 should be fabricated to be as light as possible relative to the fluid mass, as long as the material of the test cell 14 is compatible with the fluid and the expected testing conditions. Less mass of the test cell 14 will give the fluid mass proportionally more effect and better torque measurement.

By non-invasively tracking the kinematic change in mass distribution of a sample of the fluid, the apparatus 10 would eliminate the need for multiple tests, as well as be able to track the rate at which sag was occurring. This is done by measuring the change in rotational inertia over time of the sample with no initial density gradient and an original center of mass 20 coincident with the lateral axis 18 and pivot 16. The apparatus 10 would allow for the combination of several tests that currently take many days and many separate cells of fluid to be prepared. Furthermore, the same single sample can be tested over multiple time intervals to characterize the rate and nature of sag. By virtue of this single sample preparation, much less product (liquid mass) needs to be used and fewer person-hours are necessary to obtain the same amount of data, or even more data than can be obtained conventionally. Additionally, there is a large area of study that is possible when the sag profiles of fluids can be characterized in this matter. In a non-limiting example, this research could indicate whether there is a linear or non-linear rate of sag, or determine the effect of temperature and/or pressure on the rate of sag.

Advantages of the test apparatus 10 and method of using it as described herein include, but are not necessarily limited to:

Single cell preparation versus preparation of multiple cells to characterize density distribution.

Ability to observe change in density profile over time.

Cells 14 can communicate with the apparatus 10 via RFID (radio frequency identification) to allow for multiple cells 14 to be placed in the apparatus 10, and then returned to an oven. The RFID would identify each cell 14.

Another possibility for measuring time-based sag in a non-intensive method might involve a cell having a built-in set of pressure indicators aligned axially that would be sensitive enough to measure pressure differentials over height/length intervals of one inch (2.54 cm) or smaller. In one non-limiting embodiment a cell (e.g., a metal cylinder about 12 inches tall or long (30.5 cm)) could have a pressure transducer every 2 inches (5 cm) or so from the bottom to the top. As the fluid "sags", the pressure is read by the pressure transducers would be able to be correlated to the distribution of density. An advantage of such a method and apparatus would be that it would be a completely static method and would not require physical movement of any part of the apparatus. However, the costs of the apparatus and operation would be expected to be higher than those of the apparatus 10 and method described herein.

It should be noted that the apparatus 10 and method for using it as described herein is considered "non-invasive" because the test cell 14 is not opened, and does not have to be opened, during the testing procedure.

In the foregoing specification, the invention has been described with reference to specific embodiments thereof, and has been demonstrated as effective in providing an apparatus for non-invasively measuring time-based sag of a fluid mass, and methods of using it. However, it will be evident that various modifications and changes can be made thereto without departing from the broader scope of the invention as set forth in the appended claims. Accordingly, the specification is to be regarded in an illustrative rather than a restrictive sense. For example, specific test cell sizes and shapes, testing apparatus and components thereof, testing procedures and measurement techniques and conditions falling within the claimed parameters, but not specifically identified or tried in a particular composition or method or proportion or conditions, are expected to be within the scope of this invention.

The words "comprising" and "comprises" as used throughout the claims is interpreted as "including but not limited to".

The present invention may suitably comprise, consist or consist essentially of the elements disclosed and may be practiced in the absence of an element not disclosed. For instance, an apparatus for non-invasively determining time-based sag of a fluid mass may consist essentially of or consist of a test cell having an inner chamber; a support stand having a pivot rotatably engaging the test cell, where the test cell rotates about a lateral axis intersecting the pivot; a rotator configured to rotate the test cell about the pivot, the rotation being from a first point and a second point; and a torque sensor configured to estimate a torque value associated with the test cell at at least one point during rotation inclusively between the first point and the second point, where the torque value represents a change in a location of a center of mass of the fluid mass.

Alternatively, in a treated fluid composition, there may be provided a non-invasive method for measuring time-based sag in a fluid that consists essentially of or consists of providing a test cell having an inner chamber, where the inner chamber contains a liquid comprising mass, where the test cell comprises an original center of mass when the test cell is in an initial vertical position; after a time period sufficient for fluid sag to occur, rotating the test cell to an angle with respect to vertical from a first point to at least one point between the first point and a second point; measuring the torque of an angular moment of inertia about the original center of mass; and using the measured torque to determine the distance from the center of rotation to a resultant center of mass, the distance being directly proportional to time-based sag.

As used herein, the singular forms "a," "an," and "the" are intended to include the plural forms as well, unless the context clearly indicates otherwise.

As used herein, the term "and/or" includes any and all combinations of one or more of the associated listed items.

As used herein, relational terms, such as "first," "second," "top," "bottom," "upper," "lower," "over," "under," etc., are used for clarity and convenience in understanding the disclosure and do not connote or depend on any specific preference, orientation, or order, except where the context clearly indicates otherwise.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" in reference to a given parameter is inclusive of the stated value and has the meaning dictated by the context (e.g., it includes the degree of error associated with measurement of the given parameter).

What is claimed is:

1. A non-invasive method for measuring time-based sag in a fluid having a mass, the method comprising:
   providing a test cell that contains the fluid, where the test cell comprises an original center of mass and a lateral axis extending through the original center of mass;
   after a time period sufficient for fluid sag to occur, rotating the test cell about the lateral axis from an initial vertical position to a non-vertical position;
   measuring the static torque required to hold the test cell at the non-vertical position; and
   using the measured torque to determine the distance from the original center of mass to a resultant center of mass, the distance being directly proportional to time-based sag.

2. The method of claim 1 where the test cell is filled with the fluid such that the test cell has no vapor space.

3. The method of claim 1 where the step of rotating the test cell comprises rotating the test cell about the lateral axis less than 90°.

4. The method of claim 1 comprising comparing the measured torque to a set of reference standards determining displacement of the center of mass.

5. The method of claim 1 where the fluid is a drilling fluid.

* * * * *